(12) United States Patent
Vogel

(10) Patent No.: US 8,922,067 B2
(45) Date of Patent: Dec. 30, 2014

(54) RELUCTANCE AND LORENTZ-FORCE-OPERATED LINEAR DRIVE

(75) Inventor: Walter Vogel, Trossingen (DE)

(73) Assignee: Karl Storz GmbH & Co. KG (DE)

(*) Notice: Subject to any disclaimer, the term of this patent is extended or adjusted under 35 U.S.C. 154(b) by 257 days.

(21) Appl. No.: 13/035,509

(22) Filed: Feb. 25, 2011

(65) Prior Publication Data

US 2011/0210689 A1 Sep. 1, 2011

(30) Foreign Application Priority Data

Feb. 26, 2010 (DE) .................. 10 2010 000 583

(51) Int. Cl.
| | | |
|---|---|---|
| H02K 41/035 | (2006.01) | |
| A61B 1/00 | (2006.01) | |
| H02K 41/03 | (2006.01) | |
| H02K 7/08 | (2006.01) | |
| H02K 7/106 | (2006.01) | |
| H02K 7/14 | (2006.01) | |
| H02K 1/27 | (2006.01) | |

(52) U.S. Cl.
CPC ............ *H02K 41/031* (2013.01); *A61B 1/0016* (2013.01); *H02K 7/08* (2013.01); *A61B 1/00158* (2013.01); *H02K 7/106* (2013.01); *H02K 7/14* (2013.01); *H02K 1/2713* (2013.01); *A61B 1/00188* (2013.01)
USPC .................... 310/12.25; 310/12.02; 310/12.33

(58) Field of Classification Search
USPC .......... 310/12.02, 12.15, 12.24–12.26, 12.33, 310/14, 15, 17
See application file for complete search history.

(56) References Cited

U.S. PATENT DOCUMENTS

| | | | | |
|---|---|---|---|---|
| 3,981,245 | A | * 9/1976 | Buzzell et al. | 102/209 |
| 4,785,816 | A | * 11/1988 | Dow et al. | 600/446 |
| 5,478,650 | A | 12/1995 | Davanloo et al. | |
| 6,002,184 | A | 12/1999 | Delson et al. | |
| 6,157,100 | A | * 12/2000 | Mielke | 310/13 |
| 7,365,768 | B1 | 4/2008 | Ono et al. | |
| 8,278,785 | B2 | * 10/2012 | Schrader et al. | 310/12.24 |
| 2008/0310037 | A1 | 12/2008 | Kuo et al. | |
| 2009/0218892 | A1 | * 9/2009 | Schrader et al. | 310/12.24 |

FOREIGN PATENT DOCUMENTS

| | | |
|---|---|---|
| DE | 2621272 A1 | 11/1976 |
| DE | 3717872 A1 | 12/1988 |
| DE | 19618355 A1 | 11/1997 |
| DE | 10323629 A1 | 10/2004 |
| DE | 102006006877 A1 | 8/2007 |
| DE | 102008038926 A1 | 2/2009 |
| EP | 2034594 A2 | 3/2009 |
| JP | 2007089382 A | 4/2007 |

* cited by examiner

*Primary Examiner* — Dang Le (74) *Attorney, Agent, or Firm* — St. Onge Steward Johnston & Reens LLC (57) ABSTRACT

A linear motor for optical systems, for example, endoscopes, is described. The motor has a stator with a magnetic guiding member and a coil. The armature of the motor includes two permanent magnets which are of opposite polarity. A pole piece made of soft-magnetic material is provided between the permanent magnets. By applying current to the coil, the armature can be displaced from a rest position in the longitudinal direction.

15 Claims, 8 Drawing Sheets

RELUCTANCE AND LORENTZ-FORCE-OPERATED LINEAR DRIVE

CROSS-REFERENCE TO RELATED APPLICATIONS

This application claims priority to pending German Application No. 10 2010 000 583.5 filed on Feb. 26, 2010.

FIELD OF THE INVENTION

The invention relates to a linear motor in particular for optical systems. Such optical systems are used, for example, in endoscopes. In modern video endoscopes a camera chip and an appurtenant lens system are integrated in the endoscope tip. A miniaturized motor is required to adjust the focal length or the focus of the lens system.

BACKGROUND OF THE INVENTION

Classical endoscopes such as can be used, for example, for minimally invasive surgery, guide the image by means of rod lenses from the intracorporeal objective to the extracorporeal eyepiece. As a result of the rod lenses, the system is rigid and limited in optical quality. Modern video endoscopes use a camera chip in the endoscope tip. Such an endoscope is disclosed in U.S. Pat. No. 7,365,768 B1. This has a rigidly disposed lens in front of the camera chip. An adjustment of the focal length of the lens is not possible.

DE 196 18 355 C2 discloses a linear drive which can be integrated in endoscopes for adjusting the focal width of a lens system. For this purpose a permanent magnet is moved as an armature inside a stator coil. However, as a result of the large mass of the permanent magnet, the linear drive is sluggish. The relationship between the coil current and the armature position is not single-valued and necessitates an additional displacement sensor with positional regulation.

DE 37 17 872 C2 discloses a drive having an armature and a stator for a lens system in video cameras. The armature consists of two iron sleeves which are interconnected by a support for receiving the lens system. The stator has two coils and a single annular permanent magnet for generating the magnetic fields required for the movement between the coils. The complex structure of the drive can be readily implemented in video cameras having lens diameters in the centimeter range but is not scalable to the size required for endoscope applications in the millimeter range.

DE 103 23 629 A1 discloses a moving field linear motor which includes at least three stator coils. A phase-shifted current supply to the coils produces a moving field which effects a displacement of the armature with axial permanent magnets. An expensive control circuit is required to produce the moving field.

Known from DE 10 2008 038 926 A1 is a linear drive including two axially polarized permanent magnets in the armature. The armature is deflected by the current supply to the stator coils in the axial direction. In addition, the stable positions of the armature are achieved by the pole piece mounted in the stator so that a continuous displacement of the armature in a cladding tube is rendered possible. A disadvantage here is the dependence of the stroke and the adjusting forces on the soft-magnetic stator pole pieces, with the result that a high precision is required in the manufacture and assembly of these parts.

SUMMARY OF THE INVENTION

The embodiments are based on the object of providing a linear motor having such small dimensions that this can be inserted in endoscopes. Furthermore, the linear motor should have a defined zero point position and a reproducible deflection as a function of the control signal. In addition, the linear motor should exhibit large driving forces with small mass and thereby render possible a rapid, continuous and exact positioning of the optical system in the largest possible range. At the same time, the beam path through the optical system must not be blocked during displacement of the components. The power loss of the linear motor should be low so that little heat is produced in the tip of an endoscope. The drive should be composed of as few as possible and as geometrically simple as possible individual components for simple manufacture and assembly.

In an embodiment the linear motor includes a stator and an armature which is linearly displaceable thereto. The stator has one coil and a magnetic guiding member on the outer side which is disposed at least largely parallel to the direction of movement. The coil is disposed approximately at the centre of the magnetic guiding member in relation to the direction of movement. The armature is surrounded, at least partially, by the coil and has a first permanent magnet and a second permanent magnet. A pole piece is disposed between the two permanent magnets.

The length of the magnetic guiding member approximately corresponds to the length of the armature between the outer sides of the permanent magnets. It is particularly advantageous if the length of the magnetic guiding member is slightly larger, in particular between 0 percent and 10 percent larger than the length of the armature.

In a further embodiment the linear motor includes a stator and an armature which is linearly displaceable thereto. The stator has one coil and on its outer side, a magnetic guiding member which is disposed at least largely parallel to the direction of movement. The coil is approximately disposed at a first end of the magnetic guiding member in relation to the direction of movement. Said coil is enclosed by the magnetic guiding member over its entire length, i.e. it does not protrude beyond the magnetic guiding member. The armature has an axially magnetized permanent magnet. A pole piece is preferably disposed at the end of the permanent magnet located in the vicinity of the coil.

Advantageously the length of the magnetic guiding member is approximately equal to the length of the armature, corresponding to the length of the permanent magnet with the optional pole piece. It is particularly favorable if the length of the magnetic guiding member is equal to the length of the armature.

The following aspects relate to both embodiments of the linear motor.

A linear motor preferably has a rotationally symmetrical armature and/or a rotationally symmetrical stator. Further preferably the beam path of an optical system can then run through the sleeve. In particular, a lens or another optical element can sit in the sleeve. Consequently, the focal length and/or the focus of the optical system can be adjusted by a displacement of the sleeve.

The linear motor enables an exact adjustment of the position of the armature relative to the stator between two end positions. In the linear motor a unique position of the armature in relation to the stator corresponds to each coil current. Consequently, the armature can be continuously displaced in the travel range by means of an adjustment of the coil current. As a result of this unique assignment between the coil current and the armature position, the path measurements necessary according to the prior art to determine the position of the armature can be dispensed with. The individual components have a simple geometry (rings, sleeves) and therefore can easily be manufactured and assembled.

The pole piece and the magnetic guiding member must always include ferromagnetic and/or soft magnetic materials.

The linear motor can easily be miniaturized up to a size of a few millimeters external diameter. In a motor having an external diameter of a few millimeters, the travel distance between the two end positions of the armature is typically about 1 to 3 mm.

In a further advantageous embodiment there is a sliding layer between the stator and the armature. The sliding layer can compensate for unevennesses on the side of the stator facing the armature.

In an alternative embodiment, the linear motor described can be implemented with a flat stator, e.g. having a plate-shaped structure and a likewise flat or plate-shaped pole piece of the armature.

A linear motor can also consist of solid material and have a plunger at one end for the nanopositioning of instruments. Such a device can preferably be used in molecular biology, microelectronics or neurosurgery.

It is particularly favorable if the coil is supplied with a direct current with a superposed alternating current of small amplitude and having a frequency up to a maximum of 1 kHz. The static and sliding friction can be reduced by this means.

A further embodiment relates to a method for operating a linear motor, wherein the linear motor is supplied with a direct current and a superposed alternating current of small amplitude and having a frequency up to a maximum of 1 kHz. The static friction or sliding friction in the interior of the motor can be reduced by this means.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Figure 1:
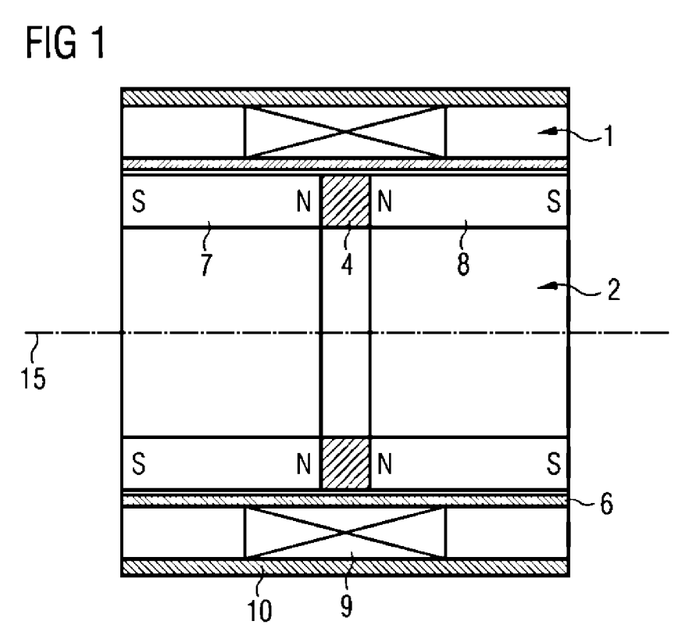
FIG. 1 shows schematically a linear motor.

FIG. 1 shows schematically an exemplary embodiment of a linear motor in cylindrical design in a sectional view. The stator 1 includes a magnetic guiding member 10 in the form of a tube, a coil 9 being disposed in the bore whereof. The magnetic guiding member preferably consists of soft magnetic material, like a ferromagnetic material. Said coil is enclosed by the magnetic guiding member over its entire length, i.e. it does not project beyond the magnetic guiding member. A sliding sleeve 6 terminates the stator 9 here towards the inside and provides a sliding layer for the armature. The sliding sleeve must consist of a non-ferromagnetic material. The armature 2 is surrounded, at least partially, by the coil and has a first permanent magnet and a second permanent magnet. Here the armature 2 includes two oppositely magnetized permanent magnets 7, 8 and an interposed pole piece 4, which enables a defined emergence of the magnetic fields of the permanent magnets through the coil in the direction of the magnetic guiding member. In principle, the arrangement also operates without the pole piece. The force of the motor can be increased by more than an order of magnitude due to the pole piece. The two permanent magnets are axially magnetized and aligned with their polarity such that as desired the north poles or the south poles lie opposite one another.

An element to be positioned, such as an optical component, can be inserted into the bore of the armature.

The armature is axially displaceable in both directions inside the sliding sleeve. The length of the magnetic guiding member approximately corresponds to the length of the armature between the outer sides of the permanent magnets. It is particularly advantageous if the length of the magnetic guiding member is slightly larger, in particular between 0 percent and 10 percent larger than the length of the armature.

The central axis 15 is also the axis of rotation in arrangements having a rotationally symmetrical structure. The linear motor is preferably designed rotationally symmetrically with annular magnetic guiding member, pole pieces, permanent magnets and an annular coil. The armature and in particular the permanent magnets as well as the pole piece are preferably hollow-cylindrical, i.e. they have the form of a cylindrical sleeve. It is understood that the linear motor may also have any other form like planar or with a rectangular, hexagonal or elliptical cross section. It may specifically have a plate-shaped structure and a likewise flat or plate-shaped pole piece of the armature. Alternatively, a plurality of linear motors disposed around a cylinder or a polygonal body can also be provided. A stable guidance is obtained, for example, in the case of a uniform arrangement of linear motors around a cylinder.

The sliding sleeve provides a sliding layer between the stator and the armature. In order to influence the magnetic fields as little as possible, the sliding layer should consist of a non-magnetic-field-conducting material, in particular of a non-ferromagnetic material. The surface thereof preferably includes a material having a low coefficient of friction, for example, PTFE (polytetrafluorethylene), silicon nitride, silicon carbide, poly-para-xylene polymers or DLC (diamond like carbon) such as is disclosed, for example, in U.S. Pat. No. 5,478,650.

Figure 2:
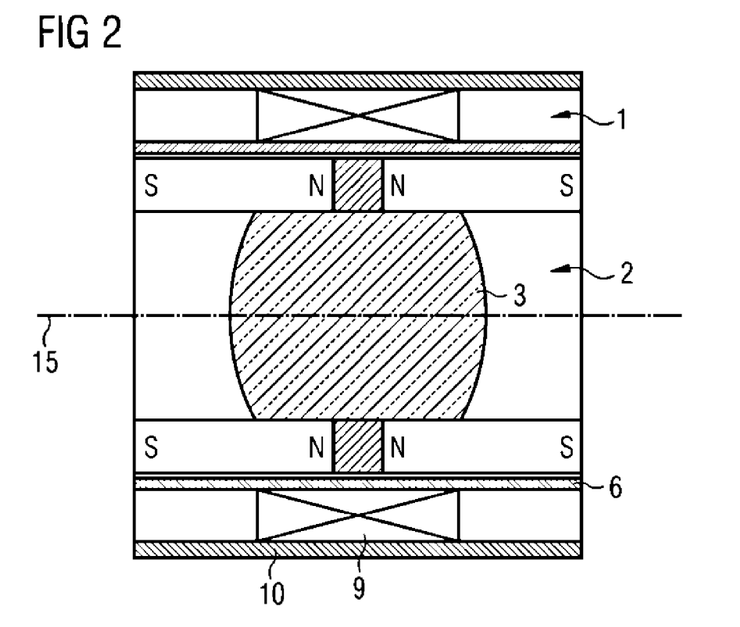
FIG. 2 shows the linear motor from FIG. 1 with a lens.

FIG. 2 shows a linear motor according to FIG. 1, wherein a lens 3 is also shown, which can be displaced by the linear motor in the direction of the central axis 15. This allows the beam path of an optical system to run through the sleeve.

Figure 3:
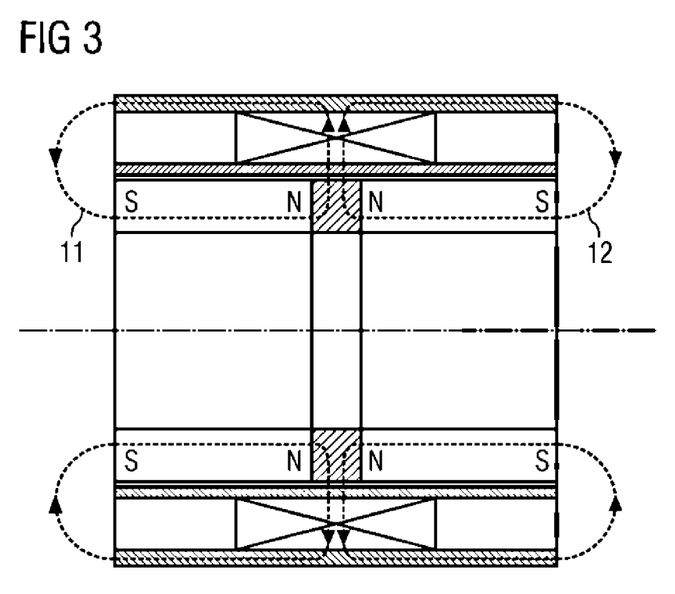
FIG. 3 shows the field behavior in the linear motor with currentless coil.

FIG. 3 shows a diagram of the linear motor with the magnetic circuits in the resting state with currentless coil. The permanent magnets each produce a magnetic flux 11, 12 which flows from the north pole of each permanent magnet 7, 8 through the pole piece 4 and in each case radially outwards through the coil 9 into the magnetic guiding member 10 of the stator. The magnetic flux goes further in the direction of the outer sides of the magnetic guiding member 10 and from there via the free air space back to the south pole of the permanent magnets 7, 8. The two magnetic circuits 11, 12 strive to minimize the length of their respective air gap in order to thereby minimize the respective magnetic reluctance of the circuit. In this case, so-called reluctance forces occur in both magnetic circuits which strive to pull the outer sides of the permanent magnets, in this case the south poles, as far as possible into the interior of the magnetic guiding member 10 and with this the air gap in order to thus reduce the magnetic reluctance. In the central position of the armature, the air gaps and therefore the reluctance forces of the two circuits are the same. With a suitable design of the length of the armature and the axial lengths of the components of the stators, a stable central position of the armature is then obtained.

If the armature is pushed out from this stable position in one of its two directions of movement as a consequence of externally acting forces, for example, acceleration forces, repelling forces act, pushing the armature back into the central position. The magnetic forces hold the armature in this position comparably to a mechanical spring.

The coil can be wound onto a coil bobbin or without a coil bobbin as desired. It can also be multi-part, i.e. it can consist of a plurality of windings.

Figure 4:
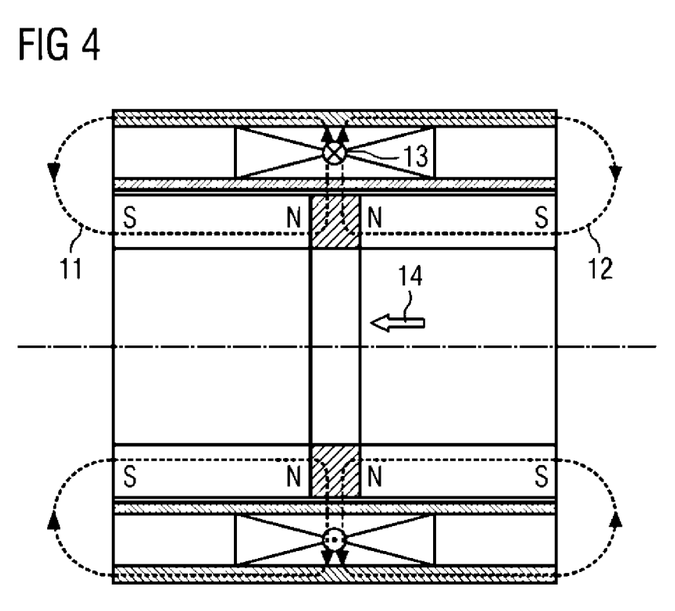
FIG. 4 shows the field behavior of the linear motor with current flowing through the coil.

FIG. 4 shows the magnetic circuits with energized coil. If the coil 9 is now energized in the direction 13 identified in FIG. 4, that is current flows through the coil, in the upper half of the cross-sectional area the current flows into the plane of the image and in the lower half, it flows out from this plane. As a result of the coil 9 being penetrated by the magnetic field from the permanent magnets 7, 8, a Lorentz force is produced. If a current flows through the coil according to the drawing, the armature 2 will be pulled to the left in direction 4 by the Lorentz force. This Lorentz force is counteracted by reluctance forces which attempt to pull the armature back into the central position. For every current through the coil 9 there is now a position of the armature in which the total of the position-dependent reluctance forces and the largely position-independent Lorentz force is zero. A stable position is established here. Consequently, there is a unique assignment between current intensity and armature position. A reversal of the current direction brings about a displacement of the armature 2 in the opposite direction. In a symmetrical structure, the movement properties in both directions are identical. It is furthermore crucial for the drive properties that the position of the armature is reproducible and stable in the desired position corresponding to the current intensity.

The direction of polarity of the magnets can also be reversed. As a result, the direction of movement for given current is reversed compared to the previously described structure. For the proper functioning of the linear motor it is merely crucial that both magnets are oppositely magnetized.

Figure 1A:
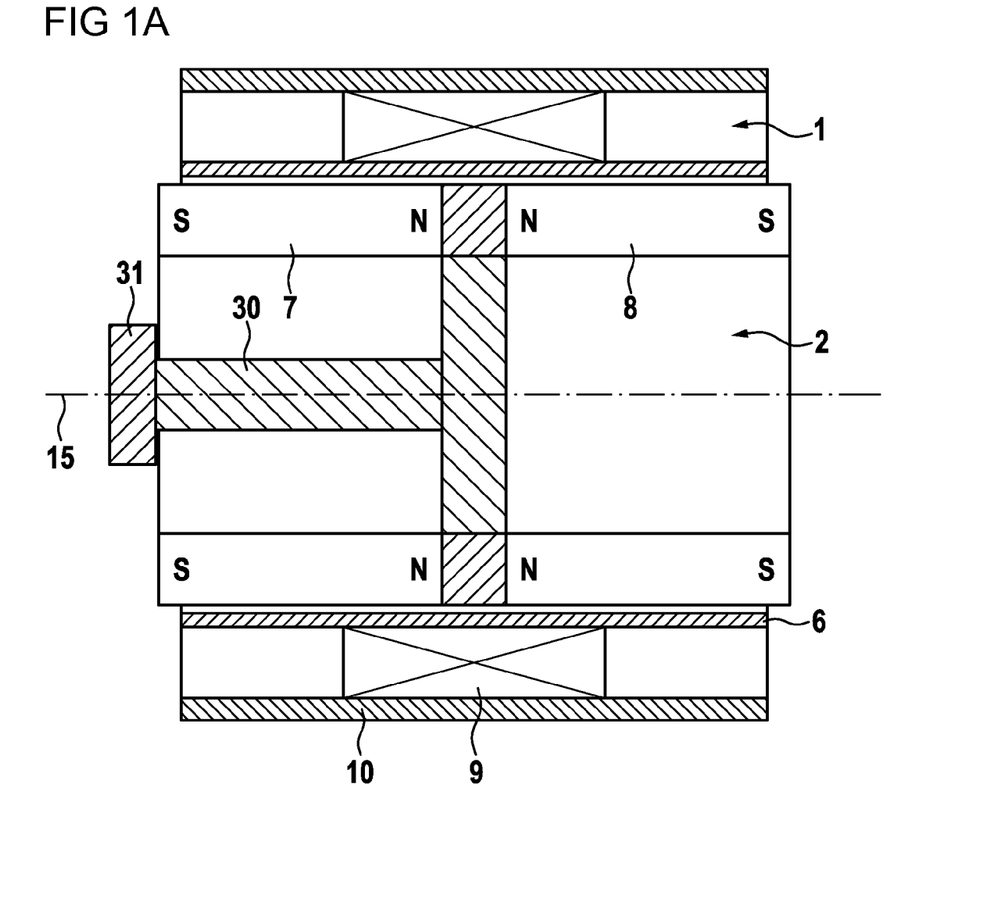
FIG. 1A shows the linear motor from FIG. 1 with a plunger at one end for the nanopositioning of an instrument.

A linear motor, as shown in FIG. 1A, can also consist of solid material and have a plunger 30 at one end for the nanopositioning of instruments 31. Such a device can preferably be used in molecular biology, microelectronics or neurosurgery.

It is particularly favorable if the coil is supplied with a direct current with a superposed alternating current of small amplitude and having a frequency up to a maximum of 1 kHz. The static and sliding friction can be reduced by this means.

Figure 5:
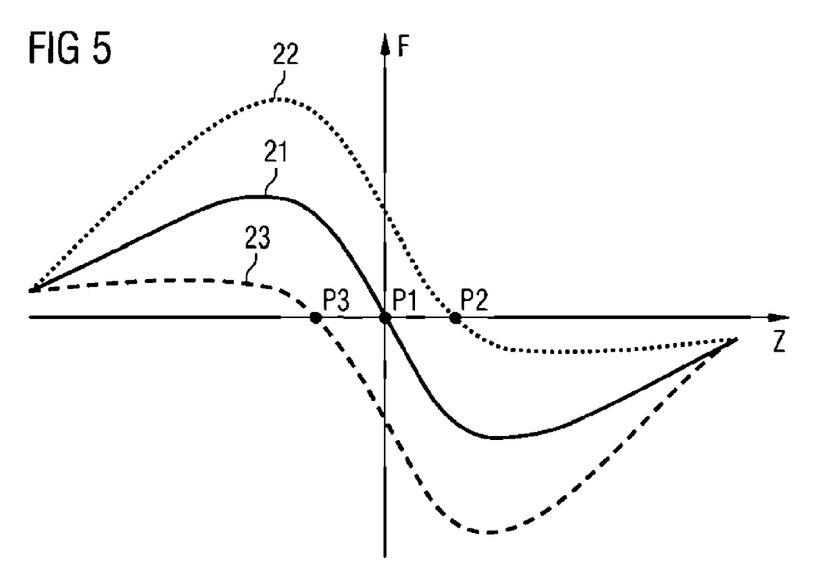
FIG. 5 shows the force behavior of the linear motor.

FIG. 5 shows in a diagram the relationship between the sum F of the forces including reluctance forces and Lorentz force as well as the position of the armature. A positive force F is plotted upwards and a positive deflection z is plotted to the right. Without energizing, the armature adopts the central position P1. If the armature is moved to the left, this receives a positive force in the direction of the z-axis, to the right, due to the reluctance forces. It will therefore attempt to preserve its central position against this force. The same applies for any deflection to the right. This force behavior is represented in the curve 21. If a current now flows in the first direction shown in FIG. 4 through the coil, a new equilibrium of reluctance forces and the Lorentz force is obtained at the point P3 as presented in the description to FIG. 4. The entire curve is thus shifted. As a result of the additional magnetic field of the coil, the reluctance forces are also reduced. Accordingly, the restoring forces in the left part of curve 23 are smaller than those in curve 21 without energizing. In the part of the curve 23 to the right of the point P3, reluctance forces and Lorentz force act in the same direction. The restoring force increases accordingly. If a current is now passed through the coil in the opposite second direction, a new equilibrium of reluctance forces and Lorentz force is obtained at the point P2 in a position of the armature to the right of the zero position. Curve 22 of the force behavior is accordingly inverted like curve 23.

Figure 6:
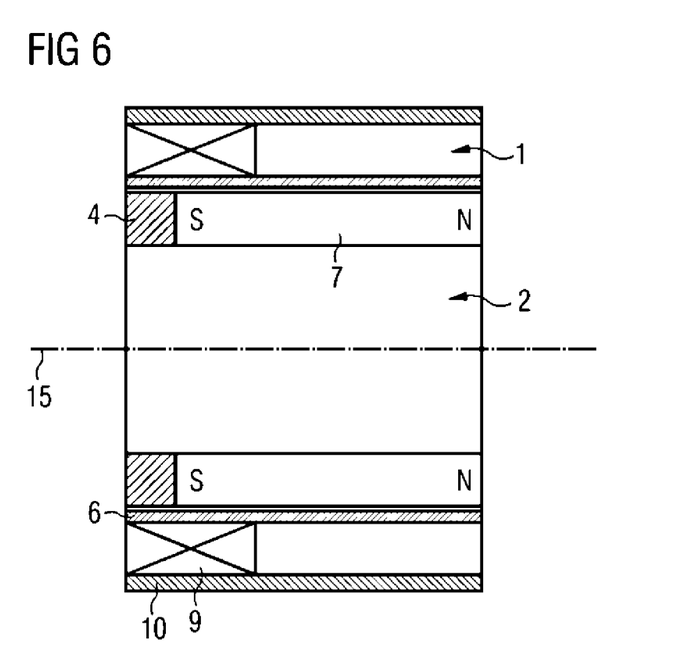
FIG. 6 shows a further variant of the linear motor.

FIG. 6 shows a further embodiment. This has a similar structure to the embodiment depicted in FIG. 1. However, the armature here only includes a first permanent magnet 7. The coil is approximately disposed at a first end of the magnetic guiding member in relation to the direction of movement. The armature here can only be moved to the right by energizing. Preferably the length of the magnetic guiding member is approximately equal to the length of the armature, corresponding to the length of the permanent magnet with the pole piece. It is particularly favorable if the length of the magnetic guiding member is equal to the length of the armature.

Figure 7:
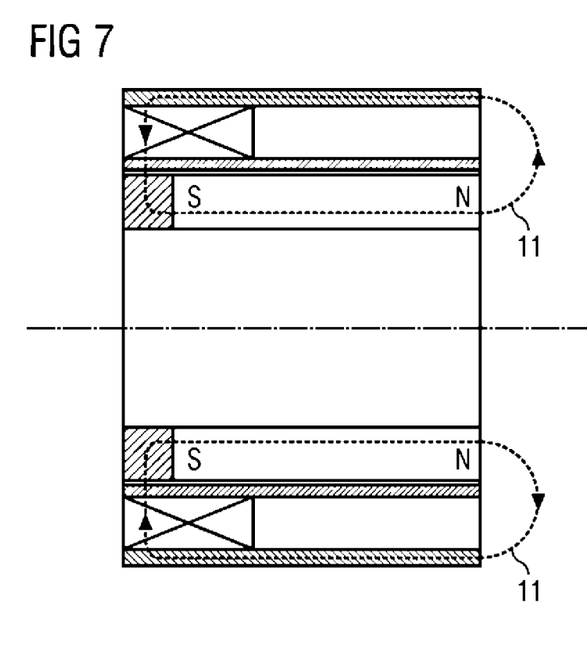
FIG. 7 shows the field behavior in the linear motor according to FIG. 6 with currentless coil.

FIG. 7 shows the behavior of the magnetic field with non-energized coil. The magnetic flux runs here in the upper part of the figure in the anticlockwise direction. A central position is established in which the reluctance forces on both sides of the armature are equal. As a result of the asymmetric arrangement with the pole piece on the left side, the armature would project slightly to the left from the stator. This can be prevented by a stop not shown here.

Figure 8:
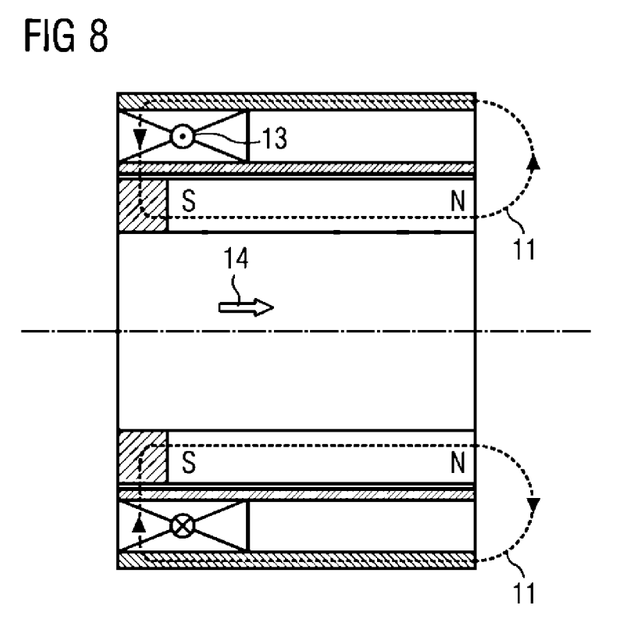
FIG. 8 shows the field behavior in the linear motor according to FIG. 6 with current flowing through the coil.

FIG. 8 shows the behavior of the magnetic field when current flows through the coil in direction 13. Here in the lower part of the coil the current flows into the plane of the drawing and emerges from the upper part of the coil from the plane of the drawing. A Lorentz force is obtained here due to the interaction of the magnetic field guided by the pole piece 4 through the coil 9 with the coil current. This Lorentz force again acts in the opposite direction to the reluctance forces so that a coil current-dependent point with force equilibrium is also obtained here.

It will be appreciated to those skilled in the art having the benefit of this disclosure that this invention is believed to provide linear motors. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A linear motor comprising:
a stator having a single coil and a cylindrical magnetic guiding member without a stator terminal shoe, the magnetic guiding member having a first end and a second end, the coil being enclosed by the magnetic guiding member over its entire length; and
an armature which is surrounded, at least partially, by the coil and which linearly displaces parallel to the stator, the armature comprising a first permanent magnet and a second permanent magnet of opposite polarity, as well as a pole piece between the two permanent magnets, the armature being distant from the magnetic guiding member by at least a thickness of the coil;
wherein the length of the armature approximately corresponds to the length of the magnetic guiding member of the stator;
wherein displacement of the armature is linearly proportional to an electrical current through the coil;
wherein in a currentless state of the coil a magnetic flux flows from sides of the permanent magnets distant to the pole piece to the ends of the magnetic guiding member.

2. The linear motor according to claim 1, wherein the length of the armature is between 0 percent and 10 percent greater than the length of the magnetic guiding member.

3. The linear motor according to claim 1, wherein an optical element is accommodated in the interior of the armature.

4. The linear motor according to claim 1, wherein the armature is rotationally symmetrical.

5. The linear motor according to claim 1, wherein the stator is rotationally symmetrical.

6. The linear motor according to claim 1, wherein a sliding sleeve comprising a material having a low coefficient of friction on the surface is disposed between stator and armature.

7. The linear motor according to claim 1, wherein the armature consists of solid material and has a plunger for the nanopositioning of instruments.

8. A method for operating a linear motor according to claim 1, wherein a very small alternating current having frequencies up to a maximum of 1 kHz is superposed on the direct current through the coil to reduce the static and sliding friction.

9. A linear motor comprising:
a stator having a single coil and a cylindrical magnetic guiding member without a stator terminal shoe the magnetic guiding member having a first end and a second end, the coil being enclosed by the magnetic guiding member over its entire length; and
an armature which is surrounded, at least partially, by the coil and which linearly displaces parallel to the stator, the armature comprising a permanent magnet and a pole piece made of soft-magnetic material on one side of the permanent magnet, the armature being distant from the magnetic guiding member by at least a thickness of the coil;
wherein an optical element is accommodated in the interior of the armature and the length of the armature approximately corresponds to the length of the magnetic guiding member of the stator;
wherein displacement of the armature is linearly proportional to an electrical current through the coil;
wherein a magnetic flux from a side of the permanent magnet distant from the pole piece and a magnetic flux from the pole piece flow into the ends of the magnetic guiding member.

10. The linear motor according to claim 9, wherein the length of the armature is between 0 percent and 10 percent greater than the length of the magnetic guiding member.

11. The linear motor according to claim 9, wherein the armature is rotationally symmetrical.

12. The linear motor according to claim 9, wherein the stator is rotationally symmetrical.

13. The linear motor according to claim 9, wherein a sliding sleeve comprising a material having a low coefficient of friction on the surface is disposed between stator and armature.

14. The linear motor according to claim 9, wherein the armature consists of solid material and has a plunger for the nanopositioning of instruments.

15. A method for operating a linear motor according to claim 9, wherein a very small alternating current having frequencies up to a maximum of 1 kHz is superposed on the direct current through the coil to reduce the static and sliding friction.

* * * * *